(12) United States Patent
Naito

(10) Patent No.: US 8,858,551 B2
(45) Date of Patent: Oct. 14, 2014

(54) HIGH-FREQUENCY TREATMENT APPARATUS

(75) Inventor: Kimihiko Naito, Musashino (JP)

(73) Assignee: Olympus Medical Systems Corp. (JP)

( * ) Notice: Subject to any disclaimer, the term of this patent is extended or adjusted under 35 U.S.C. 154(b) by 730 days.

(21) Appl. No.: 12/417,732

(22) Filed: Apr. 3, 2009

(65) Prior Publication Data

US 2009/0254084 A1 Oct. 8, 2009

(30) Foreign Application Priority Data

Apr. 8, 2008 (JP) ................................. 2008-100709

(51) Int. Cl.
*A61B 18/18* (2006.01)
*A61B 18/14* (2006.01)

(52) U.S. Cl.
CPC ..... *A61B 18/1492* (2013.01); *A61B 2018/1425* (2013.01); *A61B 18/1477* (2013.01)
USPC .................... 606/45; 606/46; 606/41; 606/32

(58) Field of Classification Search
CPC .................. A61B 18/1492; A61B 2018/1742; A61B 2018/1472
USPC .................... 606/45, 41, 32, 46; 607/101–102
See application file for complete search history.

(56) References Cited

U.S. PATENT DOCUMENTS 5,906,615 A * 5/1999 Thompson ....................... 606/45
6,015,381 A * 1/2000 Ouchi ............................ 600/104

2006/0178657 A1 * 8/2006 Sugita et al. ...................... 606/1
2006/0184048 A1 * 8/2006 Saadat ........................... 600/478
2007/0179491 A1 * 8/2007 Kratoska et al. ................ 606/32

FOREIGN PATENT DOCUMENTS

| JP | 7-265329 | 10/1995 |
|---|---|---|
| JP | 2002-301088 | 10/2002 |
| JP | 2004-167081 | 6/2004 |
| JP | 2006-212110 | 8/2006 |

(Continued)

OTHER PUBLICATIONS

European Search Report dated Jul. 27, 2009 in corresponding European Patent Application No. EP 09 00 5171 (English language).

(Continued)

*Primary Examiner* — Edelmira Bosques
(74) *Attorney, Agent, or Firm* — Ostrolenk Faber LLP

(57) ABSTRACT

A high-frequency treatment apparatus includes an insertion portion, a covering portion provided in a distal end portion of the insertion portion, an electrode portion provided in the covering portion, through which high-frequency current is to flow, including a side treatment portion arranged along an outer surface of the covering portion and a distal end treatment portion formed of a distal end portion of the electrode portion, and configured to be moved between a forward position where the distal end treatment portion is protruded from the covering portion with respect to a forward and backward movement direction and a backward position where the distal end treatment portion is arranged within the covering portion with respect to the forward and backward movement direction, and an operation member inserted through the insertion portion and connected to the electrode portion wherein the electrode portion is configured to be moved by operating the operation member.

9 Claims, 7 Drawing Sheets

(56) References Cited

FOREIGN PATENT DOCUMENTS

| | | |
|---|---|---|
| JP | 20006-218015 | 8/2006 |
| JP | 2006-333995 | 12/2006 |
| JP | 2007-117532 | 5/2007 |
| JP | 2007-275625 | 10/2007 |
| JP | 2008-029667 | 2/2008 |
| WO | WO 00/12009 | 3/2000 |
| WO | WO 2007/144004 | 12/2007 |

OTHER PUBLICATIONS

Letter from German associate dated Jul. 29, 2009 forwarding the European Search Report dated Jul. 27, 2009 to Japanese associate, including discussion of relevancy thereof. German associate's letter dated Jul. 29, 2009 was date stamped received by Japanese associate on Aug. 3, 2009 (English language).
Office Action issued by the Chinese Patent Office on Jul. 14, 2010 in connection with corresponding Chinese Patent Application No. 200910134022.6, pp. 1-4.
English translation of Chinese Office Action issued in connection with Chinese Patent Application No. 200910134022.6 on Jul. 14, 2010, pp. 1-10.
Office Action issued by the Japanese Patent Office on Oct. 23, 2012 in connection with corresponding Japanese Patent Application No. 2008-100709.
English translation of Japanese Office Action issued in connection with Japanese Patent Application No. 2008-100709 on Oct. 23, 2012.

* cited by examiner

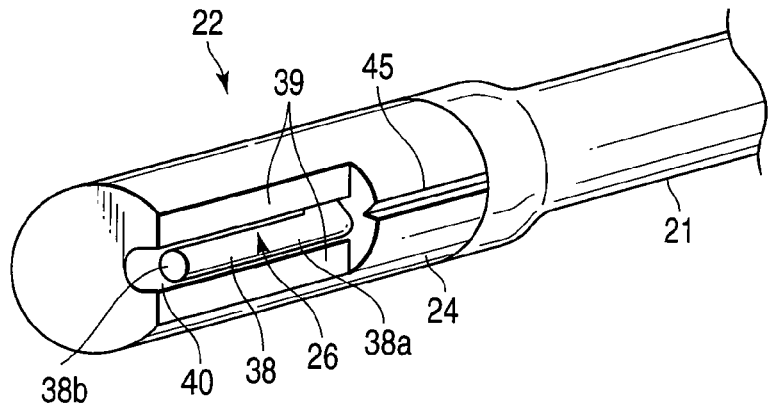
F I G. 2 A
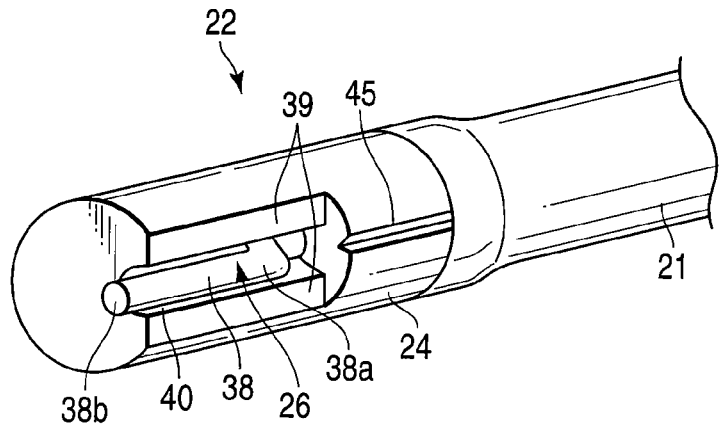
F I G. 2 B
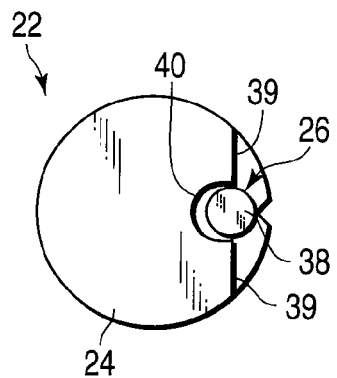
F I G. 3

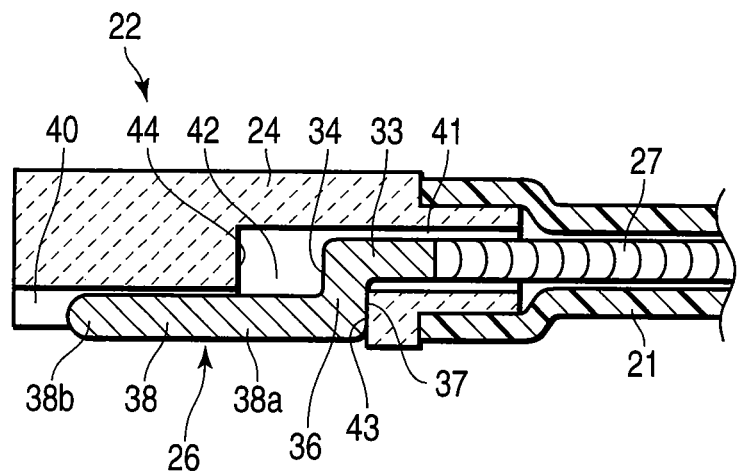
F I G. 4 A
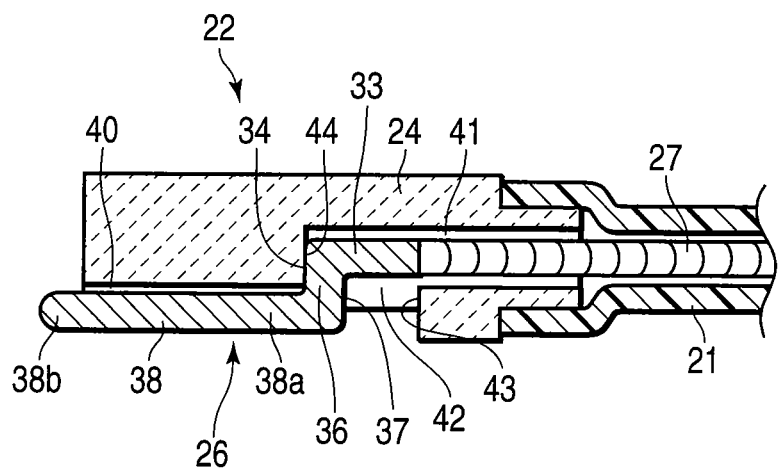
F I G. 4 B

US 8,858,551 B2

HIGH-FREQUENCY TREATMENT APPARATUS

CROSS-REFERENCE TO RELATED APPLICATIONS

This application is based upon and claims the benefit of priority from prior Japanese Patent Application No. 2008-100709, filed Apr. 8, 2008, the entire contents of which are incorporated herein by reference.

BACKGROUND OF THE INVENTION

1. Field of the Invention

The present invention relates to a high-frequency treatment apparatus configured to perform treatment to living tissue utilizing high-frequency current.

2. Description of the Related Art

Jpn. Pat. Appln. KOKAI Publication Nos. 7-265329, 2007-275625, 2002-301088, and 2007-117532 disclose high-frequency accessories configured to be used for various uses.

In particular, Jpn. Pat. Appln. KOKAI Publication Nos. 2007-275625, 2002-301088, and 2007-117532 disclose the high-frequency accessories configured to be used for endoscopic demucosation. In the endoscopic demucosation, a part containing a lesion part in a mucosal layer is resected under observation with the endoscope. That is, the surface of the mucosal layer is spot-cauterized, and markings are formed so as to surround a target part for resection of the mucosal layer. Next, a saline solution and the like are locally injected into a submucous layer under the target part for the resection, and therefore the submucous layer is distended. Then, the mucosal layer is incised along the whole periphery of the target part for the resection according to the marking, and the submucous layer is exposed. Further, the submucous layer under the target part for the resection is incised, and therefore the target part for the resection is resected.

In the high-frequency accessory disclosed in Jpn. Pat. Appln. KOKAI Publication No. 2007-275625, a rood-like electrode member is configured to be projected from and be retracted into the distal end portion of a flexible sheath in an axial direction. The marking, the incision treatment and the resection treatment can be performed to living tissue with the electrode member protruded from the flexible sheath and through which high-frequency current flows.

In the high-frequency accessory disclosed in Jpn. Pat. Appln. KOKAI Publication No. 2002-301088, a high-frequency knife is configured to be projected from and be retracted into the distal end portion of an elongated insertion portion in an axial direction. In the high-frequency knife, a spherical distal end insulation portion is attached to the distal end portion of a rood-like knife portion. The incision treatment and the resection treatment can be performed to living tissue with the knife portion of the high-frequency knife protruded from the insertion portion and through which high-frequency current flows.

In the high-frequency accessory disclosed in Jpn. Pat. Appln. KOKAI Publication No. 2007-117532, a wire-like high-frequency electrode extends in an axial direction in the side surface of the distal end portion of a tube. The resection treatment can be performed to living tissue with the high-frequency electrode through which high-frequency current flows.

BRIEF SUMMARY OF THE INVENTION

In an aspect of the present invention, a high-frequency treatment apparatus includes: an insertion portion; a covering portion provided in a distal end portion of the insertion portion; an electrode portion provided in the covering portion, through which high-frequency current is to flow, including a side treatment portion arranged along an outer surface of the covering portion and a distal end treatment portion formed of a distal end portion of the electrode portion, and configured to be moved between a forward position where the distal end treatment portion is protruded from the covering portion with respect to a forward and backward movement direction and a backward position where the distal end treatment portion is arranged within the covering portion with respect to the forward and backward movement direction; and an operation member inserted through the insertion portion and connected to the electrode portion wherein the electrode portion is configured to be moved by operating the operation member.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a perspective view showing a treatment unit in an electrode backward movement state according to the first embodiment of the present invention;

FIG. 2B is a perspective view showing the treatment unit in an electrode forward movement state according to the first embodiment of the present invention;

FIG. 3 is a front view showing the treatment unit according to the first embodiment of the present invention;

FIG. 4A is a longitudinal cross-sectional view showing the treatment unit in the electrode backward movement state according to the first embodiment of the present invention;

FIG. 4B is a longitudinal cross-sectional view showing the treatment unit in the electrode forward movement state according to the first embodiment of the present invention;

DETAILED DESCRIPTION OF THE INVENTION

FIGS. 1 to 5C show a first embodiment of the present invention.

Figure 1:
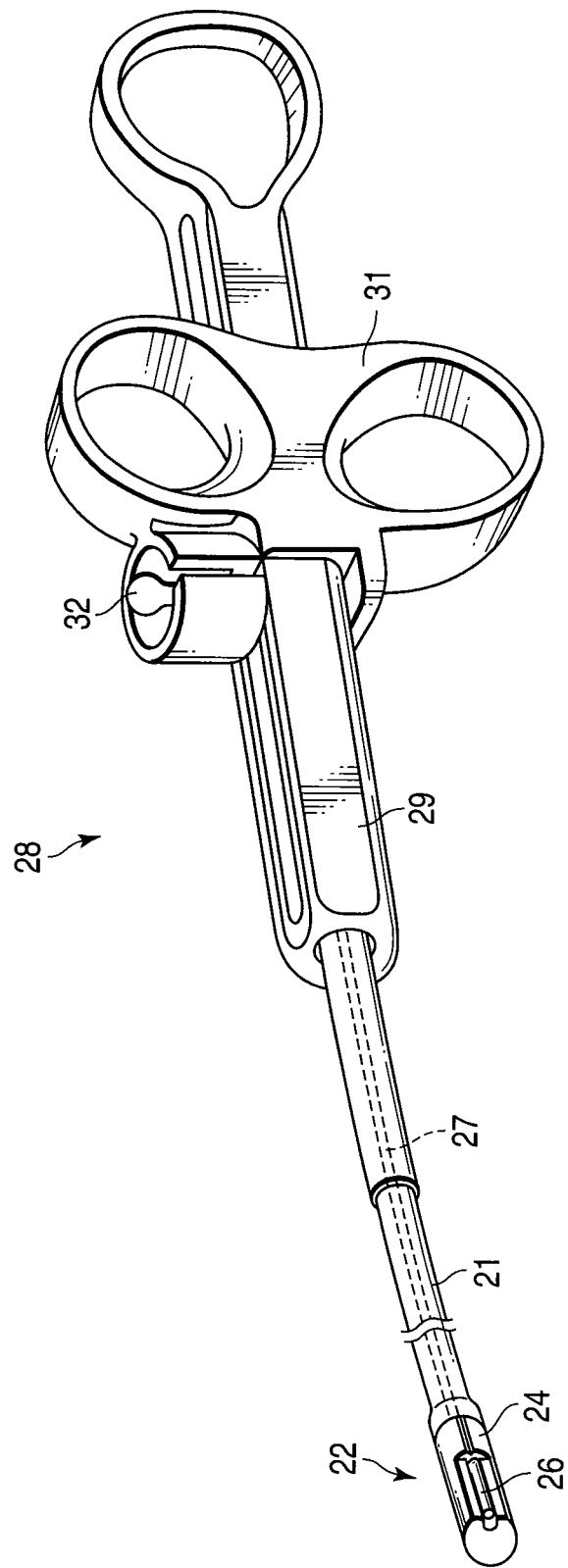
FIG. 1 is a perspective view showing a high-frequency accessory according to a first embodiment of the present invention.

Referring to FIG. 1, the schematic configure of a high-frequency accessory as a high-frequency treatment apparatus will be described.

The high-frequency accessory includes a flexible sheath 21 as an insertion portion configured to be inserted into the interior of the body through an accessory channel in an endoscope. A treatment unit 22 is provided in the distal end portion of the flexible sheath 21. In the treatment unit 22, an electrode member 26 as an electrode portion is provided in a distal end cover 24 as the covering portion, and the electrode member 26 is movable forward and backward with respect to the distal end cover 24 in a longitudinally axial direction of the flexible sheath 21. The distal end portion of an electrode wire 27 as an operation member is connected to the proximal end portion of the electrode member 26. The electrode wire 27 is inserted through the flexible sheath 21 and is movable forward and backward with respect to the flexible sheath 21 in the longitudinally axial direction of the flexible sheath 21. An operation portion 28 is coupled to the proximal end portion of the flexible sheath 21 and is configured to be held and operated by an operator. In the operation portion 28, a slider 31 is provided in an operation portion body 29, and the slider 31 is movable forward and backward in the longitudinally axial direction of the operation portion 28 with respect to the operation portion body 29. The electrode wire 27 inserted through the flexible sheath 21 is put into the operation portion body 29 and then is coupled to the slider 31. When operating the slider 31 to be moved forward and backward with respect to the operation portion body 29, the electrode wire 27 is moved forward and backward with respect to the flexible sheath 21, and therefore the electrode member 26 is moved forward and backward with respect to the distal end cover 24. In addition, a plug 32 is provided in the slider 31, and the electrode wire 27 is electrically connected to the inner end portion of the plug 32. The outer end portion of the plug 32 is configured to be connected to the apparatus body through an electric cable. High-frequency current flows through the electrode member 26 via the electric cable, the plug 32 and the electrode wire 27 from the apparatus body. Here, the electrode wire 27 and the electrode member 26 is made of metal and the like having conductivity, the distal end cover 24 is made of ceramic and so on which is insulation, and the flexible sheath 21 is made of resin and the others which is insulation.

Referring to FIGS. 2A to 4B, the treatment unit 22 will be described in detail.

From the proximal end of the electrode member 26 to the distal end thereof, the electrode member 26 extends in the longitudinally axial direction of the flexible sheath 21, and then bents outwardly in a wide direction orthogonal to the longitudinally axial direction, and then extends outwardly in the wide direction, and again bents distally in the longitudinally axial direction, and then extends distally in the longitudinally axial direction. In other word, in the electrode member 26, a supporting portion 33 extending in the longitudinally axial direction, a forward movement limiting portion 34 formed of the bending part on the proximal end side, a connecting portion 36 extending in the wide direction, the backward movement limiting portion 37 formed of the bending part on the distal end side and the treatment portion 38 extending in the longitudinally axial direction is provided from the proximal end side to the distal end side. A side treatment portion 38a is formed of the whole treatment portion 38 and a distal end treatment portion 38b is formed of the distal end portion of the treatment portion 38.

The distal end cover 24 has a substantially round columnar shape, and the proximal end portion of the distal end cover 24 is coaxially inserted into and fixed to the distal end portion of the flexible sheath 21. A plane surface portion 39 is formed by D-cut on the distal end side of the outer peripheral portion of the distal end cover 24 and is orthogonal to the wide direction of the distal end cover 24. A placement portion 40 has a shape of a groove and extends from the distal end of the distal end cover 24 in the longitudinally axial direction in the plane surface portion 39. On the other hand, a passage portion 41 has a shape of a penetrating hole and is formed in the proximal end side portion of the distal end cover 24 along the central axis of the distal end cover 24. An interconnecting portion 42 has a shape of a slot and is formed between the proximal end side part of the placement portion 40 and the distal end side part of the passage portion 41 in the distal end cover 24. The proximal end wall of the placement portion 40 forms a backward movement limiting receiving portion 43 and the distal end wall of the passage portion 41 forms a forward movement limiting receiving portion 44. It is noted that a mark 45 has a shape of a V-shaped groove and extends in the longitudinally axial direction in the proximal end side portion of the outer peripheral portion of the distal end cover 24. The mark 45 is aligned with the placement portion 40 with respect to a peripheral direction. The supporting portion 33 of the electrode member 26 is inserted through the passage portion 41 of the distal end cover 24, the connecting portion 36 extends across the interconnecting portion 42, and the treatment portion 38 extends along the placement portion 40. As is shown in FIG. 3, the widely directionally inner side portion of the treatment portion 38 is housed in the placement portion 40 and the widely directionally outer side portion of the treatment portion 38 is protruded from the plane surface portion 39 with respect to the wide direction and is not protruded from the circularly peripheral surface forming the most outer periphery of the distal end cover 24.

Moreover, the supporting portion 33, the coupling portion 36, and the treatment portion 38 of the electrode member 26 are movable forward and backward in the longitudinally axial direction in the passage portion 41, the interconnecting portion 42 and the placement portion 40 of the distal end cover 24, respectively, and so the electrode member 26 is movable forward and backward in the longitudinally axial direction with respect to the distal end cover 24. As is shown in FIGS. 2B and 4B, when the forward movement limiting portion 34 formed of the bending part on the proximal end side of the electrode member 26 is contacted with the forward movement limiting receiving portion 44 formed of the distal end wall of the passage portion 41 of the distal end cover 24, a forward movement of the electrode member 26 is limited, and the electrode member 26 is positioned in a forward position. When the electrode member 26 is arranged in the forward position, the distal end treatment portion 38b on the distal end portion of the treatment portion 38 is protruded from the distal end cover 24 with respect to the longitudinally axial direction as a forward and backward movement direction. On the other hand, as is shown in FIGS. 2A and 4A, when the backward movement limiting portion 37 formed of the bending part on the distal end side of the electrode member 26 is contacted with the backward movement limiting receiving portion 43 formed of the proximal end wall of the placement portion 40 of the distal end cover 24, a backward movement of the electrode member 26 is limited, and the electrode member 26 is positioned in a backward position. When the electrode member 26 is arranged in the backward position, the distal end treatment portion 38b is arranged within the distal end cover 24 with respect to the longitudinally axial direction. It is noted that the mark 45 is aligned with the placement portion 40 with respect to the peripheral direction and indicates arrangement of the treatment portion 38 of the electrode member 26 in the distal end cover 24.

Figure 5A:
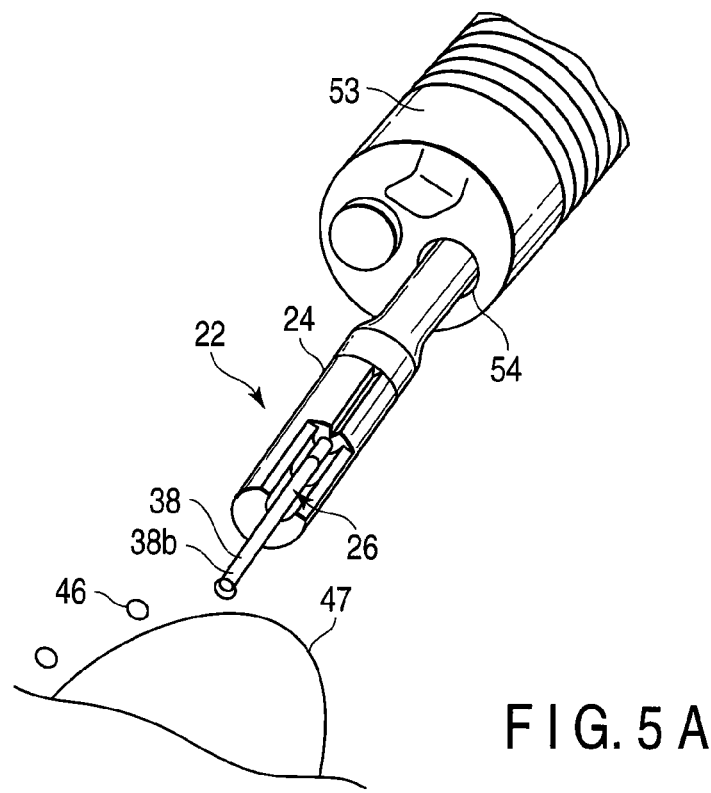
FIG. 5A is a perspective view showing marking with the high-frequency accessory according to the first embodiment of the present invention.
Figure 5B:
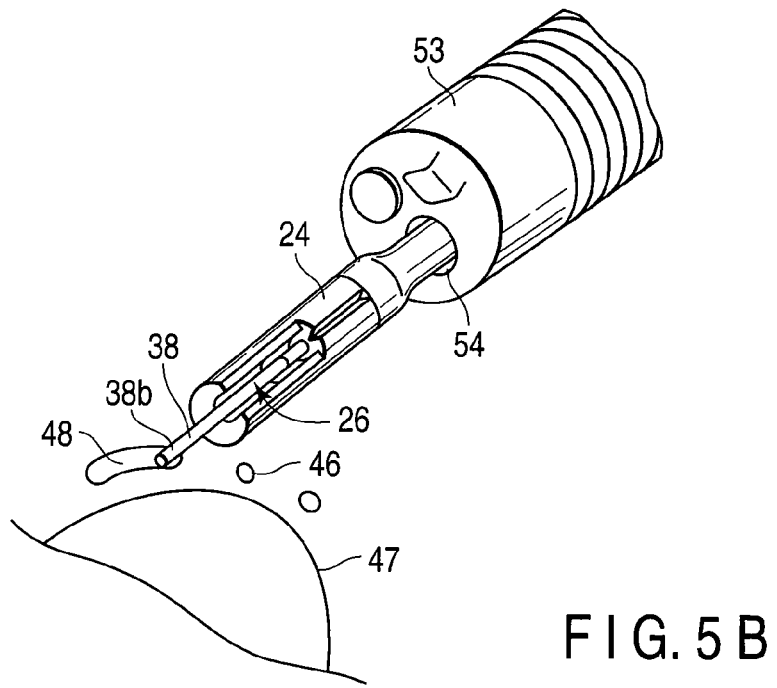
FIG. 5B is a perspective view showing incision treatment with the high-frequency accessory according to the first embodiment of the present invention.
Figure 5C:
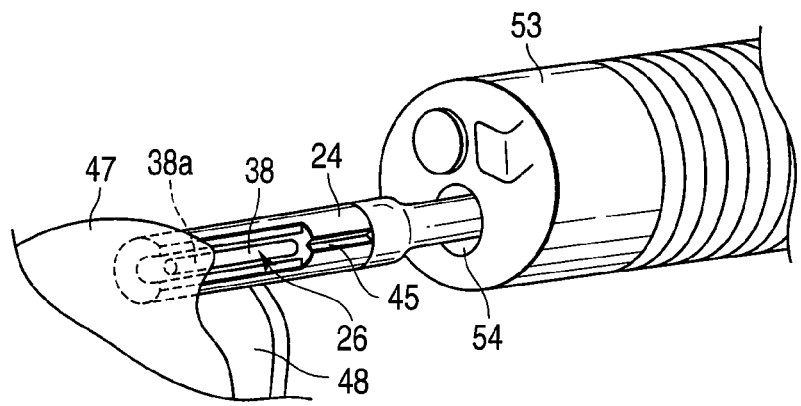
FIG. 5C is a perspective view showing resection treatment with the high-frequency accessory according to the first embodiment of the present invention.

Referring to FIGS. 5A to 5C, a method for using the high-frequency accessory according to the present embodiment will be described taking endoscopic demucosation as an example.

A endoscope 53 is inserted into the interior of the body and the interior of the body is observed. In the case where a lesion part is found in a mucosal layer 47, the endoscopic demucosation is performed and a part containing the lesion part in the mucosal layer 47 is resected. Hereinafter, the endoscopic demucosation will be described dividing it into each step.

Marking

Referring to FIG. 5A, the treatment unit 22 of the high-frequency accessory is inserted into the interior of the body through the accessory channel 54 of the endoscope 53. The slider 31 is operated to be moved forward with respect to the operation portion body 29 in the operation portion 28, and therefore, through the electrode wire 27, the electrode member 26 is moved forward with respect to the distal end cover 24. The forward movement limiting portion 34 of the electrode member 26 is contacted with the forward movement limiting receiving portion 44 of the distal end cover 24, the electrode member 26 is positioned in the forward position, and the distal end treatment portion 38b of the electrode member 26 is protruded from the distal end cover 24 with respect to the longitudinally axial direction. Next, the apparatus body is actuated, and high-frequency current flows through the electrode member 26 via the electrode wire 27. Then, the treatment unit 22 is appropriately moved by operating the operation portion 28 to be moved forward and backward and operating the bending portion of the endoscope 53 to be actuated to be bent, and therefore the distal end treatment portion 38b is touched with the surface of the mucosal layer 47 and the surface of the mucosal layer 47 is cauterized, whereby forming a marking 46. A plurality of markings 46 is formed so as to surround a target part for resection such that the target part for the resection in the mucosal layer 47 can be easily recognized.

Local Injection

A hollow puncture needle is inserted into the interior of the body through the accessory channel 54 of the endoscope 53. The puncture needle is punctured into a submucous layer 48 under the target part for the resection in the mucosal layer 47, a saline solution and the like is locally injected into the submucous layer 48 through the puncture needle, and therefore the submucous layer 48 is distended and the target part for the resection is elevated.

Incision Treatment

Referring to FIG. 5B, the treatment unit 22 is inserted into the interior of the body, the electrode member 26 is arranged in the forward position, and high-frequency current flows through the electrode member 26. After that, the distal end treatment portion 38b is touched to the mucosal layer 47 and is moved along the markings, and therefore the whole periphery of the target part for the resection of the mucosal layer 47 is incised and the submucous layer 48 is exposed.

Resection Treatment

Referring to FIG. 5C, the slider 31 is operated to be moved backward with respect to the operation portion body 29 in the operation portion 28, and therefore, through the electrode wire 27, the electrode member 26 is moved backward with respect to the distal end cover 24. The backward movement limiting portion 37 of the electrode member 26 is contacted with the backward movement limiting receiving portion 43 of the distal end cover 24, and therefore the electrode member 26 is positioned in the backward position and the distal end treatment portion 38b of the electrode member 26 is arranged within the distal end cover 24 with respect to the longitudinally axial direction. Then, high-frequency current flows through the electrode member 26. After that, the treatment unit 22 is moved in the wide direction and the widely directionally outer side portion of the side treatment portion 38a formed of the whole treatment portion 38 is contacted with the submucous layer 48, and therefore the submucous layer 48 is incised, and the target part for the resection of the mucosal layer 47 is resected. When the treatment portion 38 of the electrode member 26 is covered with the mucosal layer 47 and so on to be disabled to be visually recognized during the resection, a direction of the treatment portion 38 is recognized on the basis of the mark 45 of the distal end cover 24, and then the treatment is performed. Here, since the distal end treatment portion 38b is arranged within the distal end cover 24 with respect to the longitudinally axial direction and the widely directionally outer side portion of the side treatment portion 38a formed of the whole treatment portion 38 is protruded from the distal end cover 24 with respect to the wide direction, the incision is performed when moving the treatment unit 22 in the wide direction. Therefore, no submucous layer is incised in an unintentional direction, and also no muscularis under the submucous layer 48 is incised. In addition, since the widely directionally outer side portion of the treatment portion 38 is not protruded from the circularly peripheral surface forming the most outer periphery of the distal end cover 24, the submucous layer 48 is not excessively incised and no muscularis is incised even when the whole plane surface portion 39 of the distal end cover 24 is pressed on the submucous layer 48.

The high-frequency accessory according to the present embodiment includes following effects.

In the high-frequency accessory according to the present embodiment, when the electrode member 26 is arranged in the forward position and the distal end treatment portion 38b is protruded from the distal end cover 24 with respect to the longitudinally axial direction, it is possible to appropriately perform the marking and the incision treatment to living tissue with the distal end treatment portion 38b. Moreover, when the electrode member 26 is arranged in the backward position and the distal end treatment portion 38b is arranged within the distal end cover 24 with respect to the longitudinally axial direction, it is possible to appropriately perform the resection treatment to living tissue with the widely directionally outer side portion of the side treatment portion 38a formed of the whole treatment portion 38 arranged along the outer surface of the distal end cover 24. In this way, the single high-frequency accessory suitable for all of the marking, the incision treatment and the resection treatment is realized.

Moreover, it is possible to position the electrode member 26 in the forward position or the backward position by operating the slider 31 to be moved forward or backward with respect to the operation portion body 29 in the operation portion 28 to move the electrode wire 27 forward or backward through the electrode member 26 to bring the forward movement limiting portion 34 or the backward movement limiting portion 37 of the electrode member 26 in contact with the forward movement limiting receiving portion 44 or the backward movement limiting receiving portion 43 of the distal end cover 24. This improves an operability of the high-frequency accessory.

Furthermore, it is possible to recognize a direction of the treatment portion 38 on the basis of the mark 45 of the distal end cover 24 even when the treatment portion 38 is covered with the mucosal layer and the others to be disabled to be visually recognized during the resection. This improves an operability of the high-frequency accessory.

FIGS. 6A to 8B shows a second embodiment of the present invention.

In a treatment portion 38 of an electrode member 26 according to the present embodiment, from the proximal end of the treatment portion 38 to the distal end thereof, the treatment portion 38 extends in a longitudinally axial direction of a flexible sheath 21, and then bent inwardly in a wide direction, and then extends inwardly in the wide direction. In the treatment portion 38, a side treatment portion 38a is formed of the whole proximal end side part extending in the longitudinally axial direction of the treatment portion 38, and a distal end treatment portion 38b having a shape of a hook is formed of the distal end of the proximal end side part and the distal end side part extending in the wide direction of the treatment portion 38. In addition, in the electrode member 26, a bending part on the middle portion of the electrode member 26 does not form a backward movement limiting portion 37, and the distal end side part of the treatment portion 38 forms a backward movement limiting portion 37.

On the other hand, a housing portion 49 has a shape of a groove, is continuous with a placement portion 40, and extends inwardly in the wide direction from the edge of the distal end surface of a distal end cover 24 in the distal end surface of the distal end cover 24. In addition, in the distal end cover 24, the proximal end wall of the placement portion 40 does not form a backward movement limiting receiving portion 43, and the button wall of the housing portion 49 forms the backward movement limiting receiving portion 43.

Figure 6A:
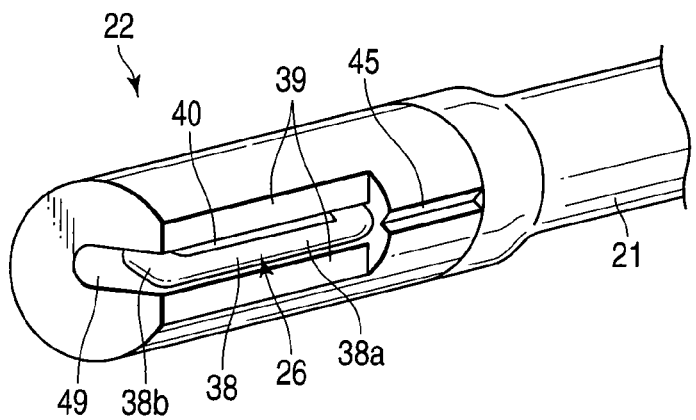
FIG. 6A is a perspective view showing a treatment unit in an electrode backward movement state according to a second embodiment of the present invention.
Figure 6B:
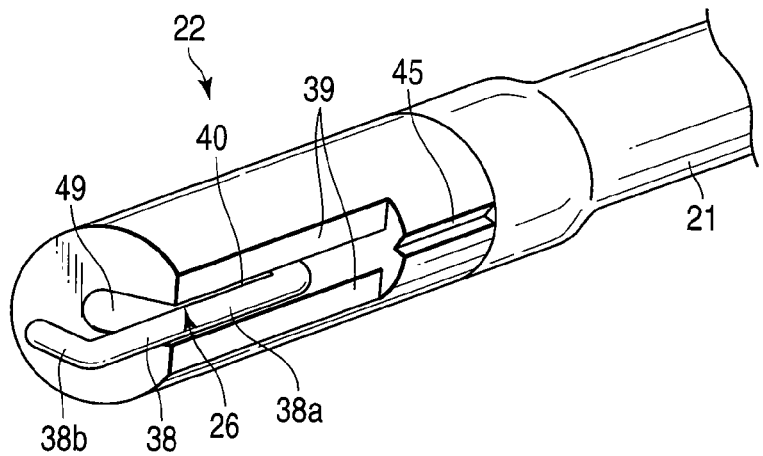
FIG. 6B is a perspective view showing the treatment unit in an electrode forward movement state according to the second embodiment of the present invention.
Figure 7:
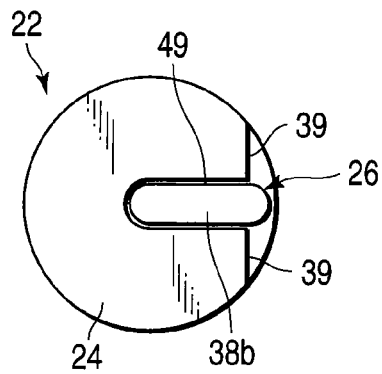
FIG. 7 is a front view showing the treatment unit according to the second embodiment of the present invention.
Figure 8A:
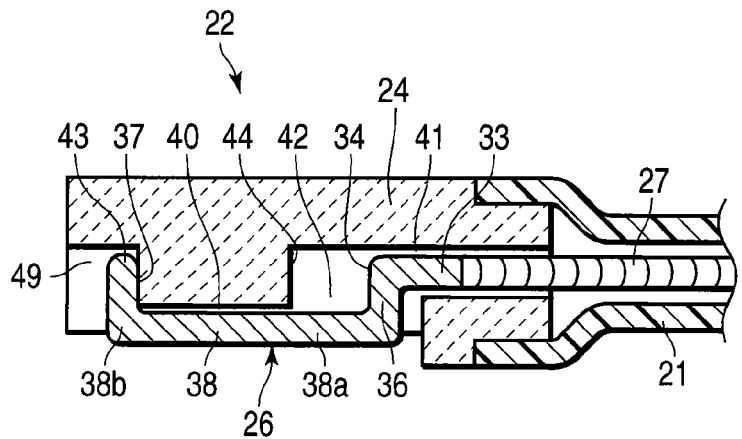
FIG. 8A is a longitudinal cross-sectional view showing the treatment unit in the electrode backward movement state according to the second embodiment of the present invention.
Figure 8B:
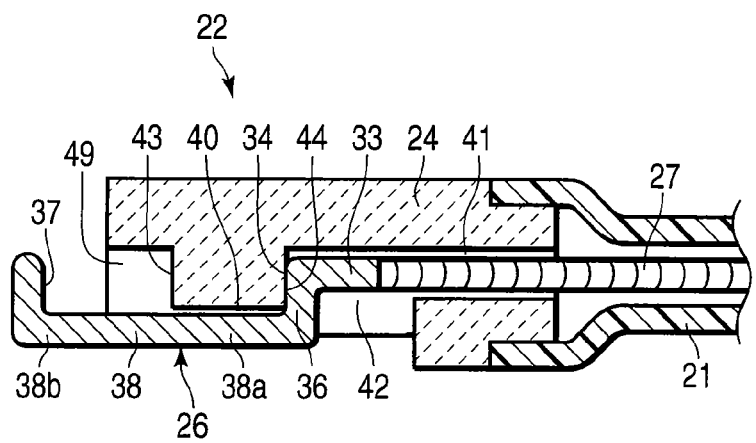
FIG. 8B is a longitudinal cross-sectional view showing the treatment unit in the electrode forward movement state according to the second embodiment of the present invention.

As is shown in FIGS. 6B and 8B, when the electrode member 26 is arranged in a forward position, the distal end treatment portion 38b of the electrode member 26 is protruded from the distal end cover 24 with respect to the longitudinally axial direction. On the other hand, as is shown in FIGS. 6A and 8A, when the backward movement limiting portion 37 formed of the distal end side part of the treatment portion 38 is contacted with the backward movement limiting receiving portion 43 formed of the button wall of the housing portion 49 of the distal end cover 24, the electrode member 26 is positioned in the backward position. When the electrode member 26 is arranged in the backward position, the distal end side part of the treatment portion 38 is housed in the housing portion 49 and the distal end treatment portion 38b is arranged within the distal end cover 24 with respect to the longitudinally axial direction.

A method for using a high-frequency accessory according to the present embodiment is similar to the method for using the high-frequency accessory according to the first embodiment. However, in marking, it is possible to form a marking 46 with the bending part of the distal end treatment portion 38b as well as the distal end of the distal end treatment portion 38b. Furthermore, in resection treatment, in the case where there is a part which it is difficult to resect, it is possible to easily resect the part by arranging the electrode member 26 in the forward position and then hooking the distal end treatment portion 38b having the shape of the hook on the part to treat the part.

In this way, in the high-frequency accessory according to the present embodiment, since the distal end treatment portion 38b has the shape of the hook, it is possible to easily resect a part which it is difficult to resect by hooking the distal end treatment portion 38b on the part to treat the part. This improves a treatment capability of the high-frequency accessory.

It is noted that the bending part on the middle portion of the electrode member 26 may form the backward movement limiting portion 37 in the electrode member 26 and the proximal end wall of the placement portion 40 may form the backward movement limiting receiving portion 43 in the distal end cover 24, as is similar to the first embodiment.

Figure 9:
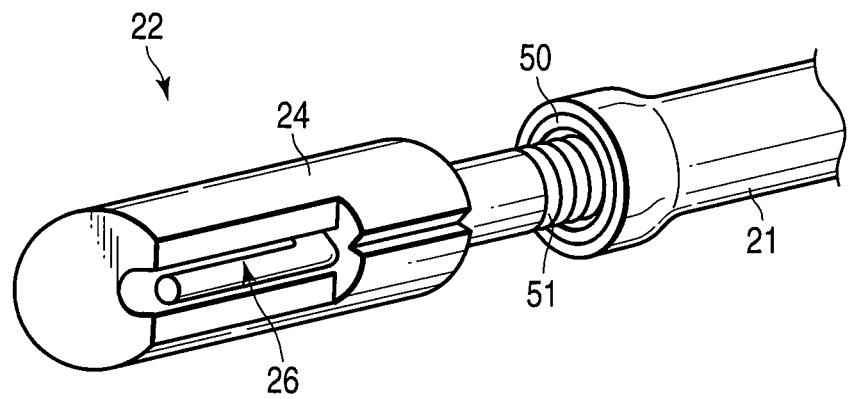
FIG. 9 is an exploded perspective view showing a treatment unit according to a third embodiment of the present invention.
Figure 10:
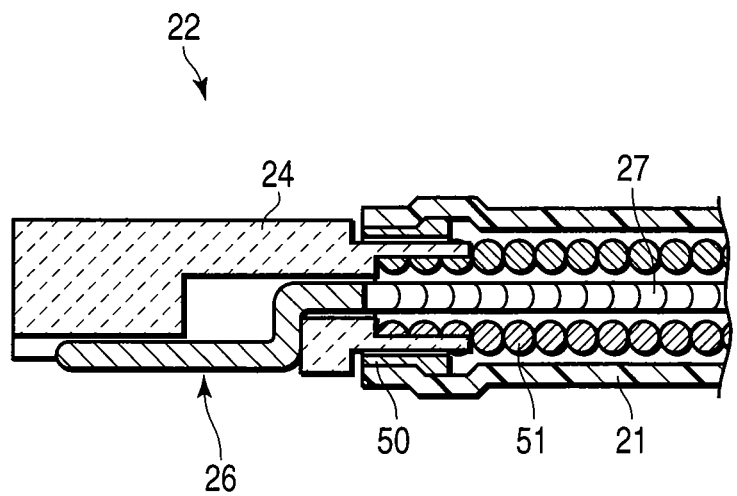
FIG. 10 is a longitudinal cross-sectional view showing the treatment unit according to the third embodiment of the present invention.

FIGS. 9 and 10 show a third embodiment of the present invention.

In a high-frequency accessory according to the present embodiment, a treatment unit 22 is rotatable about a longitudinal axis of a flexible sheath 21 with respect to the flexible sheath 21. That is, a connecter 50 has a circularly cylindrical shape, and is coaxially inserted into and fixed to the distal end portion of the flexible sheath 21. The proximal end portion of a distal end cover 24 is inserted into the connecter 50, and the proximal end portion of the distal end cover 24 is rotatable about the longitudinal axis of the flexible sheath 21 with respect to the connecter 50. The distal end portion of a coil sheath 51 as a rotational operation member is inserted into and fixed to the proximal end portion of the distal end cover 24. The coil sheath 51 is inserted through the flexible sheath 21 and is rotatable about the longitudinal axis of the flexible sheath 21 with respect to the flexible sheath 21. An electrode wire 27 is inserted through the coil sheath 51. The coil sheath 51 is coupled to a rotation knob in the operation portion 28. When operating the rotation knob to be rotated, the coil sheath 51, the distal end cover 24, the electrode member 26 and the electrode wire 27 is rotated together with one another about the longitudinal axis of the flexible sheath 21.

A method for using the high-frequency accessory according to the present embodiment is similar to the method for using the high-frequency accessory according to the first embodiment. However, in each treatment, a direction of the treatment portion 38 of the electrode member 26 is adjusted so as to be suitable for each treatment by operating the rotation knob to be rotated to rotate the treatment unit 22, appropriately.

In this way, in the present embodiment, it is possible to adjust a direction of the treatment portion 38 of the electrode member 26 so as to be suitable for treatment by operating the rotation knob to be rotated to rotate the treatment unit 22. This improves an operability of the high-frequency accessory.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency treatment apparatus comprising:
   an insertion portion having an axial direction;
   a covering portion provided in a distal end portion of the insertion portion and having a distal end and a proximal end;
   an electrode portion having a distal end and a proximal end which is provided in the covering portion, through which high-frequency current is to flow; and an operation member inserted through the insertion portion and connected to the electrode portion wherein the electrode portion is configured to be moved along the axial direction between a forward position and a backward position with respect to the covering portion by operating the operation member;

wherein:

the covering portion includes:

a plane surface portion formed on a region including the distal end of the covering portion and extending in the axial direction, and a placement portion on the plane surface portion, which has a concave groove being concave with respect to the plane surface portion, the concave groove extending in the axial direction, the electrode portion is configured to move in the axial direction in a state that a part of the electrode portion is near the concave groove of the placement portion to the plane surface portion and is housed in the placement portion and the electrode portion includes:

a distal end treatment portion formed at the distal end of the electrode portion, the distal end treatment portion distally protruding from the distal end of the covering portion with the axial direction of the insertion portion when the electrode portion is arranged in the forward position, and being arranged between the distal end and the proximal end of the covering portion with the axial direction of the insertion portion when the electrode portion is arranged in the backward position; and a side treatment portion provided at a proximal side of the distal end treatment portion and extending parallel with the axial direction, a widely directionally inner side portion of the side treatment portion being housed in the placement portion and a widely directionally outer side portion of the side treatment portion protruding outwardly with respect to the plane surface portion.

2. The high-frequency treatment apparatus according to claim 1, wherein the distal end treatment portion has a shape of a hook.

3. The high-frequency treatment apparatus according to claim 1, wherein the electrode portion includes a limiting portion, and the covering portion includes a limiting receiving portion configured to be contacted with the limiting portion to position the electrode portion in the forward position or the backward position.

4. The high-frequency treatment apparatus according to claim 1, wherein the covering portion includes a mark indicating arrangement of the side treatment portion.

5. The high-frequency treatment apparatus according to claim 1, wherein the covering portion is rotatable about a longitudinal axis of the insertion portion with respect to the insertion portion together with the electrode portion, and the high-frequency treatment apparatus further comprises a rotational operation member inserted through the insertion portion and connected to the covering portion wherein the covering portion is configured to be rotated by operating the rotational operation member.

6. The high-frequency treatment apparatus according to claim 1, wherein the entire side treatment portion is inside a most outer periphery of the covering portion.

7. The high-frequency treatment apparatus according to claim 1, wherein the covering portion has a substantially round columnar shape which defines a central axis, and the plane surface portion formed on the region including the distal end of the covering portion is formed by D-cut.

8. The high-frequency treatment apparatus according to claim 7, wherein the electrode portion includes:

a supporting portion extending in the central axis of the covering portion, a connecting portion provided on a distal end of the supporting portion and extending in a radial direction with respect to the central axis; and a treatment portion provided on a radially distal end of the connecting portion with respect to the central axis, extending parallel with the central axis and including the distal end treatment portion and the side treatment portion.

9. The high-frequency treatment apparatus according to claim 1, wherein a part of the widely directionally outer side portion of the side treatment portion protrudes outwardly with respect to the plane surface portion when the electrode portion is arranged in the backward position.

* * * * *